United States Patent
Chen et al.

(10) Patent No.: US 12,403,360 B2
(45) Date of Patent: Sep. 2, 2025

(54) INTELLIGENT EXERCISE INTENSITY ASSESSING SYSTEM AND ASSESSING METHOD THEREOF

(71) Applicant: EHUNTSUN HEALTH TECHNOLOGY CO., LTD., Taichung (TW)

(72) Inventors: Chao-Chuan Chen, Taichung (TW); Han-Pin Ho, Taichung (TW); Jong-Shyan Wang, Taichung (TW); Yu-Ting Lin, Taichung (TW); Chi-Yao Chiang, Taichung (TW); Yu-Liang Lin, Taichung (TW)

(73) Assignee: EHUNTSUN HEALTH TECHNOLOGY CO., LTD., Taichung (TW)

( * ) Notice: Subject to any disclaimer, the term of this patent is extended or adjusted under 35 U.S.C. 154(b) by 423 days.

(21) Appl. No.: 17/968,154

(22) Filed: Oct. 18, 2022

(65) Prior Publication Data

US 2024/0082642 A1 Mar. 14, 2024

(30) Foreign Application Priority Data

Sep. 12, 2022 (TW) .................................. 111134401

(51) Int. Cl.
A63B 24/00 (2006.01)

(52) U.S. Cl.
CPC ...... *A63B 24/0075* (2013.01); *A63B 24/0006* (2013.01); *A63B 24/0062* (2013.01);
(Continued)

(58) Field of Classification Search
CPC ............ A63B 2024/009–0096; A63B 24/0087
See application file for complete search history.

(56) References Cited

U.S. PATENT DOCUMENTS

| 11,412,962 | B1 * | 8/2022 | Miller | .................. | A61B 5/4845 |
| 2009/0118100 | A1 * | 5/2009 | Oliver | ................ | A63B 24/0062 |
| | | | | | 482/8 |

(Continued)

FOREIGN PATENT DOCUMENTS

| DE | 102012004698 B3 * | 7/2013 | ............. A61B 5/002 |
| WO | WO-2018044721 A1 * | 3/2018 | ......... A63B 22/0023 |

*Primary Examiner* — Nyca T Nguyen
(74) *Attorney, Agent, or Firm* — Birch, Stewart, Kolasch & Birch, LLP

(57) ABSTRACT

An intelligent exercise intensity assessing system includes an exercise testing machine, a physiological information sensor, a signal transmitter connected with the physiological information sensor, a central control host connected with the signal transmitter, and a cloud database connected with the central control host. The physiological information sensor senses physiological information of an exerciser before and after the exerciser operates the exercise testing machine. The physiological information is transmitted by the signal transmitter to the central control host, and transmitted by the central control host to the cloud database. The cloud database analyzes the physiological information to obtain a corresponding forecasted watt value, and obtains a resistance level of different fitness apparatuses according to the forecasted watt value. The intelligent exercise intensity assessing system can trace and record data of the exerciser, and obtain a suitable exercise prescription by calculation in coordination with the physiological information of the exerciser.

7 Claims, 4 Drawing Sheets

(52) U.S. Cl.
CPC ................ *A63B 2024/0012* (2013.01); *A63B 2024/0065* (2013.01)

(56) References Cited

U.S. PATENT DOCUMENTS

| | | | |
|---|---|---|---|
| 2012/0088634 A1* | 4/2012 | Heidecke | A63B 22/0005 482/92 |
| 2013/0123071 A1* | 5/2013 | Rhea | A63B 24/00 482/8 |
| 2015/0360083 A1* | 12/2015 | Lagree | A63B 23/0405 482/130 |
| 2016/0129310 A1* | 5/2016 | Ahmed | A61B 5/11 600/508 |
| 2018/0021629 A1* | 1/2018 | DeLuca | A63B 21/00069 482/4 |
| 2018/0056132 A1* | 3/2018 | Foley | A63B 23/0405 |
| 2018/0085623 A1* | 3/2018 | Flook | A63B 21/0557 |
| 2021/0086030 A1* | 3/2021 | Kashyap | G06N 20/00 |

* cited by examiner

INTELLIGENT EXERCISE INTENSITY ASSESSING SYSTEM AND ASSESSING METHOD THEREOF

BACKGROUND OF THE INVENTION

1. Field of the Invention

The present invention relates to exercise training systems and more particularly, to an intelligent exercise intensity assessing system and an assessing method thereof.

2. Description of the Related Art

The general fitness apparatuses mostly have the function of allowing the exerciser to see physiological information thereof at any time in the training process, or enabling the exerciser the training according to the exercise mode self-set by the exerciser. However, if the whole training process meets the exerciser's own need depends on only a personal cognition. The exercise intensity can't be adjusted appropriately according to the physiological information of the exerciser. Therefore, the traditional exercise training method is hard to attain great exercise effect.

SUMMARY OF THE INVENTION

It is a primary objective of the present invention to provide an intelligent exercise intensity assessing system which can obtain exercise prescriptions suitable for exercisers.

To attain the above primary objective, the intelligent exercise intensity assessing system of the present invention includes an exercise testing machine, a physiological information sensor, a signal transmitter, a central control host, and a cloud database. The exercise testing machine is adapted for an exerciser to perform an exercise test. The physiological information sensor is worn on the exerciser for sensing the physiological information of the exerciser before and after the exerciser operates the exercise testing machine. The signal transmitter is electrically connected with the physiological information sensor for receiving the physiological information sensed by the physiological information sensor. The central control host is electrically connected with the signal transmitter for collecting the physiological information received by the signal transmitter. The cloud database is electrically connected with the central control host for recording the physiological information and analyzing the physiological information. The cloud database uses the physiological information to obtain a forecasted watt value corresponding thereto and obtain a resistance level corresponding to different fitness apparatuses according to the forecasted watt value.

It can be known from the above description that the intelligent exercise intensity assessing system of the present invention can trace and record the exercise condition of the exerciser, and after analyzing the data, obtain an exercise prescription suitable for the exerciser by calculation in coordination with the physiological information of the exerciser, so as to optimize the exercise training effect for the exerciser.

Preferably, the central control host is adapted for the exerciser to create a basic information; the central control host obtains a maximum heart rate of the exerciser from the basic information.

Preferably, before the exerciser operates the exercise testing machine, the physiological information sensor obtains a resting heart rate of the exerciser; the cloud database calculates a heart rate reserve by the resting heart rate and the maximum heart rate, and uses the heart rate reserve to obtain a heart rate value of the exerciser under different training intensity.

Preferably, the heart rate reserve is obtained by subtracting the resting heart rate from the maximum heart rate. Preferably, when the training intensity is a warm-up grade, the heart rate value is RHR+(HRR×20%); when the training intensity is a low grade, the heart rate value is RHR+(HRR×40%); when the training intensity is a medium grade, the heart rate value is RHR+(HRR×60%); when the training intensity is a high grade, the heart rate value is RHR+(HRR×85%).

Preferably, when the exerciser operates the exercise testing machine, the cloud database uses a rating of perceived exertion scale (RPE scale) to obtain the physical condition of the exerciser under different heart rates.

Preferably, after the exerciser operates the exercise testing machine, the cloud database obtains a maximal oxygen uptake of the exerciser, and uses the maximal oxygen uptake and the heart rate reserve to obtain a metabolic equivalent of task (MET) of the exerciser.

Preferably, the metabolic equivalent of task is calculated by the following equation: MET=VO2max×MHRR÷3.5÷60, wherein MET is the metabolic equivalent of task, VO2max is the maximal oxygen uptake, and MHRR is the maximum of the heart rate reserve under different training intensity.

Preferably, the exercise testing machine is an exercise bike.

In another aspect, the present invention further provides an assessing method of the aforementioned intelligent exercise intensity assessing system, which includes the steps of: a) using the physiological information sensor to sense the physiological information of the exerciser before and after the exerciser operates the exercise testing machine; b) using the signal transmitter to receive the physiological information and transmit the physiological information to the central control host; c) using the central control host to transmit the physiological information to the cloud database for analysis, so that the cloud database obtains a said forecasted watt value corresponding thereto and obtains a said resistance level corresponding to different fitness apparatuses according to the forecasted watt value; and d) using the cloud database to allot the exerciser to one of the fitness apparatuses and control the fitness apparatus used by the exerciser to provide the resistance level obtained in the step c).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
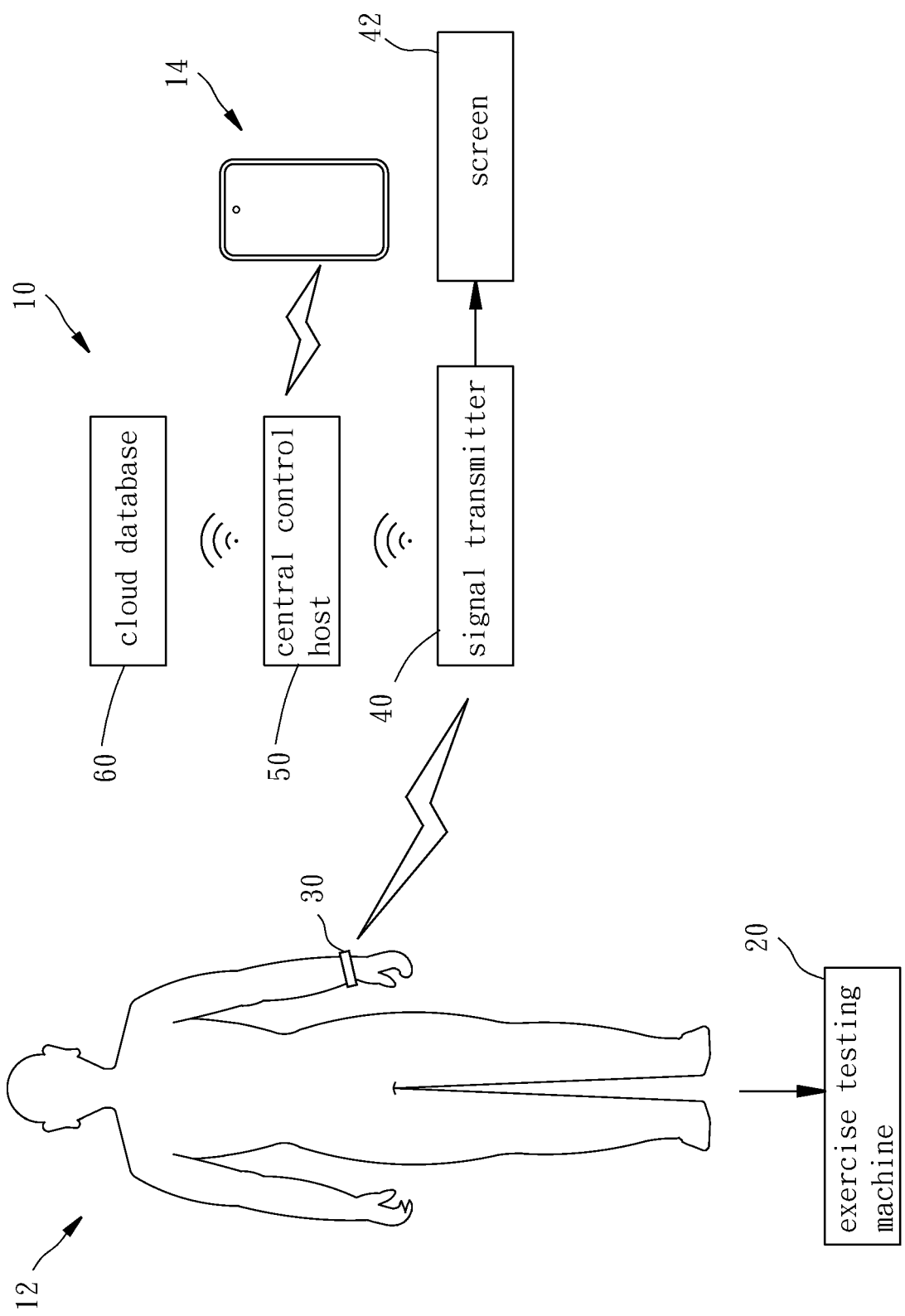
FIG. 1 is a block diagram of an intelligent exercise intensity assessing system of the present invention.

First of all, it is to be mentioned that throughout this specification, including the following embodiment and claims, the directional terms are all based on the direction shown in the figures. Besides, same reference numerals used in the following embodiment and the figures designate same or similar elements or the structural features thereof.

Referring to FIG. 1, an intelligent exercise intensity assessing system 10 of the present invention includes an exercise testing machine 20, a physiological information sensor 30, a signal transmitter 40, a central control host 50, and a cloud database 60.

The exercise testing machine 20 is adapted for an exerciser 12 to perform an exercise test. In this embodiment, the exercise testing machine 20 is an exercise bike for obtaining a forecasted maximal oxygen uptake.

The physiological information sensor 30 is worn on the exerciser 12 for sensing the physiological information of the exerciser 12 before and after the exerciser 12 operates the exercise testing machine 20. Before the exerciser 12 operates the exercise testing machine 20, the physiological information sensor 30 obtains a resting heart rate (RHR) of the exerciser 12. For example, referring to Table 1 and Table 2, the basic information and data of two different exercisers are shown in Table 1 and Table 2. In Table 1, the resting heart rate obtained when the exerciser 12 keeps motionless for a period of time (about 3 minutes) is 74 bpm. Besides, in Table 2, the resting heart rate obtained when the other exerciser 12 keeps motionless for a period of time (about 3 minutes) is 62 bpm.

Figure 2:
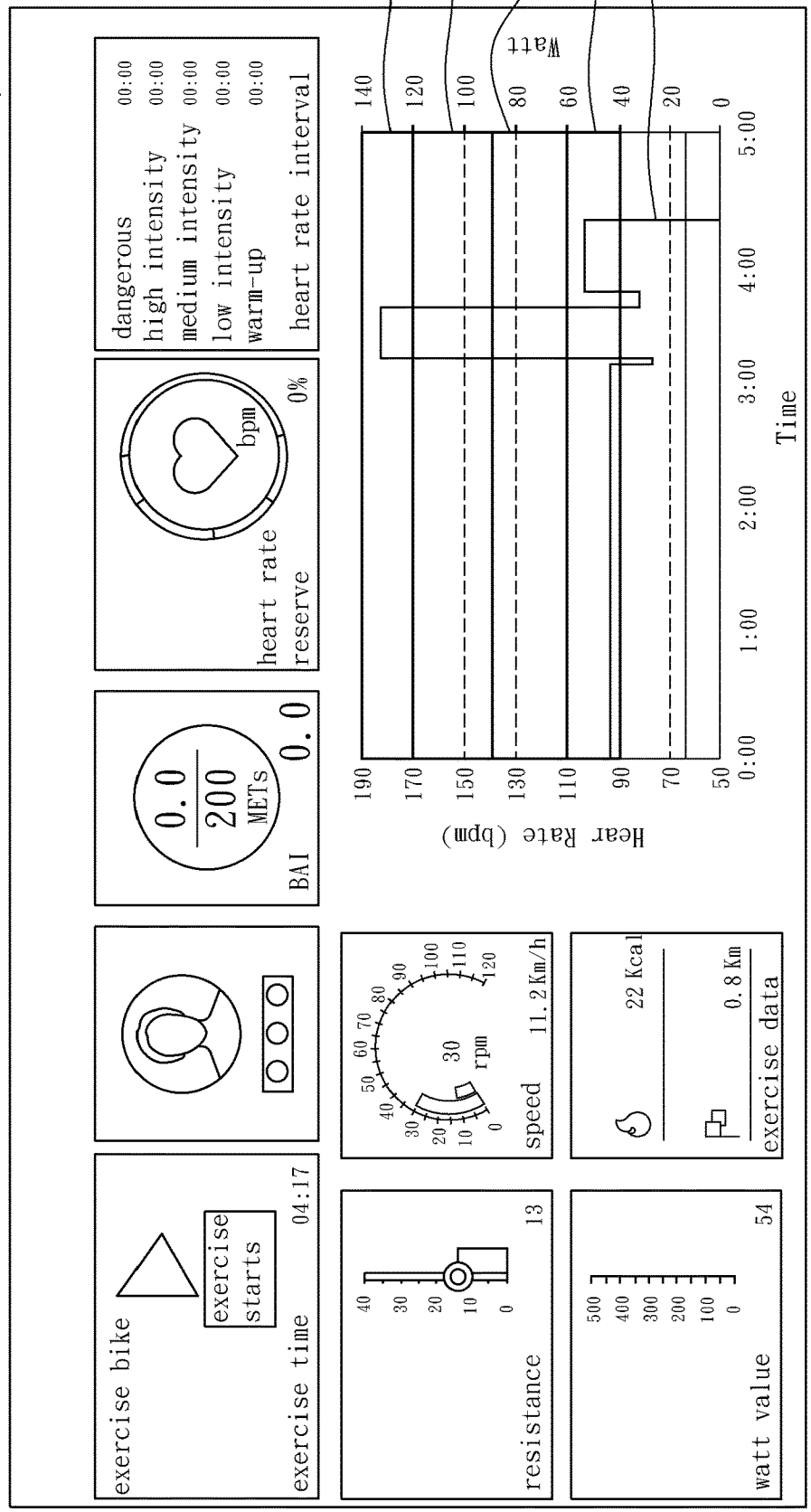
FIG. 2 is a schematic view of a system interface of an intelligent assessing system provided by an intelligent exercise training method of the present invention.

The signal transmitter 40 is a TV stick in this embodiment, but unlimited thereto. The signal transmitter 40 is connected with the physiological information sensor 30 through Bluetooth for receiving the physiological information sensed by the physiological information sensor 30 and showing the aforementioned physiological information on a screen 42 (as shown in FIG. 2).

The central control host 50 is connected with the signal transmitter 40 through Wi-Fi or Bluetooth for collecting the physiological information received by the signal transmitter 40. Besides, the central control host 50 is adapted for the exerciser 12 to create a basic information, so that the central control host 50 obtains a maximum heart rate (MHR) of the exerciser 12 from the basic information. In this embodiment, through the basic information of the exerciser 12, the central control host 50 calculates the maximum heart rate of the exerciser 12 by subtracting the age thereof from 220, i.e. by the equation MHR=220−age. For example, referring to Table 1, the exerciser is aged 48, and the maximum heart rate thereof is obtained by the calculation 220−48=172 bpm. Besides, in Table 2, the exerciser is aged 31, and the maximum heart rate thereof is obtained by the calculation 220−31=189 bpm.

The cloud database 60 is connected with the central control host 50 through Wi-Fi or Bluetooth to store the basic information created by the exerciser through the central control host 50, and record the physiological information collected by the central control host 50 and make records and analysis for the aforementioned physiological information. As a result, the cloud database 60 uses the aforementioned physiological information to obtain a forecasted watt value corresponding thereto and obtain a resistance level corresponding to different fitness apparatuses according to the forecasted watt value.

Further speaking, the cloud database 60 uses the resting heart rate (RHR) and the maximum heart rate (MHR) to calculate a heart rate reserve (HRR), and uses the heart rate reserve to obtain a heart rate value of the exerciser 12 under different training intensity. In this embodiment, the cloud database 60 obtains the heart rate reserve (HRR) by subtracting the resting heart rate (RHR) from the maximum heart rate (MHR). Besides, the training intensity includes a warm-up grade, a low grade, a medium grade, a high grade and a dangerous grade, totaling five grades (intervals). When the training intensity is the warm-up grade, the heart rate value is RHR+(HRR×20%). When the training intensity is the low grade, the heart rate value is RHR+(HRR×40%). When the training intensity is the medium grade, the heart rate value is RHR+(HRR×60%). When the training intensity is the high grade, the heart rate value is RHR+(HRR×85%).

For example, referring to Table 1, when the training intensity is the warm-up grade, the heart rate value is 74+(172−74)×20%=93.6 bpm, rounded up to 94 bpm. Besides, in Table 2, when the training intensity is the medium grade, the heart rate value is 62+(189−62)×60%=138.2 bpm, rounded down to 138 bpm. Other heart rate values are calculated in a similar fashion, not repeatedly described hereinafter.

TABLE 1

| basic information | resting heart rate (bpm) | maximum heart rate (bpm) | maximal oxygen uptake (mL/kg/min) | warm-up | low | medium | high | warm-up | low | medium | high |
|---|---|---|---|---|---|---|---|---|---|---|---|
| | | | | heart rate value (bpm) | | | | resistance level (Level) (take elliptical machine as example) | | | |
| age (years): 48 | 74 | 172 | 41.2 | 94 | 113 | 133 | 157 | 4 | 9 | 15 | 22 |
| height (cm): 171 | | | | | | | | | | | |
| weight (kg): 77 | | | | | | | | | | | |
| | | | | forecasted watt value (Watts) | | | | | | | |
| sex: male | | | | 49 | 98 | 146 | 207 | | | | |

TABLE 2

| basic information | resting heart rate (bpm) | maximum heart rate (bpm) | maximal oxygen uptake (mL/kg/min) | warm-up | low | medium | high | resistance level (Level) (take elliptical machine as example) | | | |
|---|---|---|---|---|---|---|---|---|---|---|---|
| | | | | | | | | warm-up | low | medium | high |
| | | | | heart rate value (bpm) | | | | | | | |
| age (years): 31 | 62 | 189 | 35.6 | 87 | 113 | 138 | 170 | 2 | 7 | 9 | 13 |
| height (cm): 163 | | | | | | | | | | | |
| weight (kg): 60 | | | | | | | | | | | |
| | | | | forecasted watt value (Watts) | | | | | | | |
| sex: female | | | | 32 | 64 | 95 | 135 | | | | |

Figure 3:
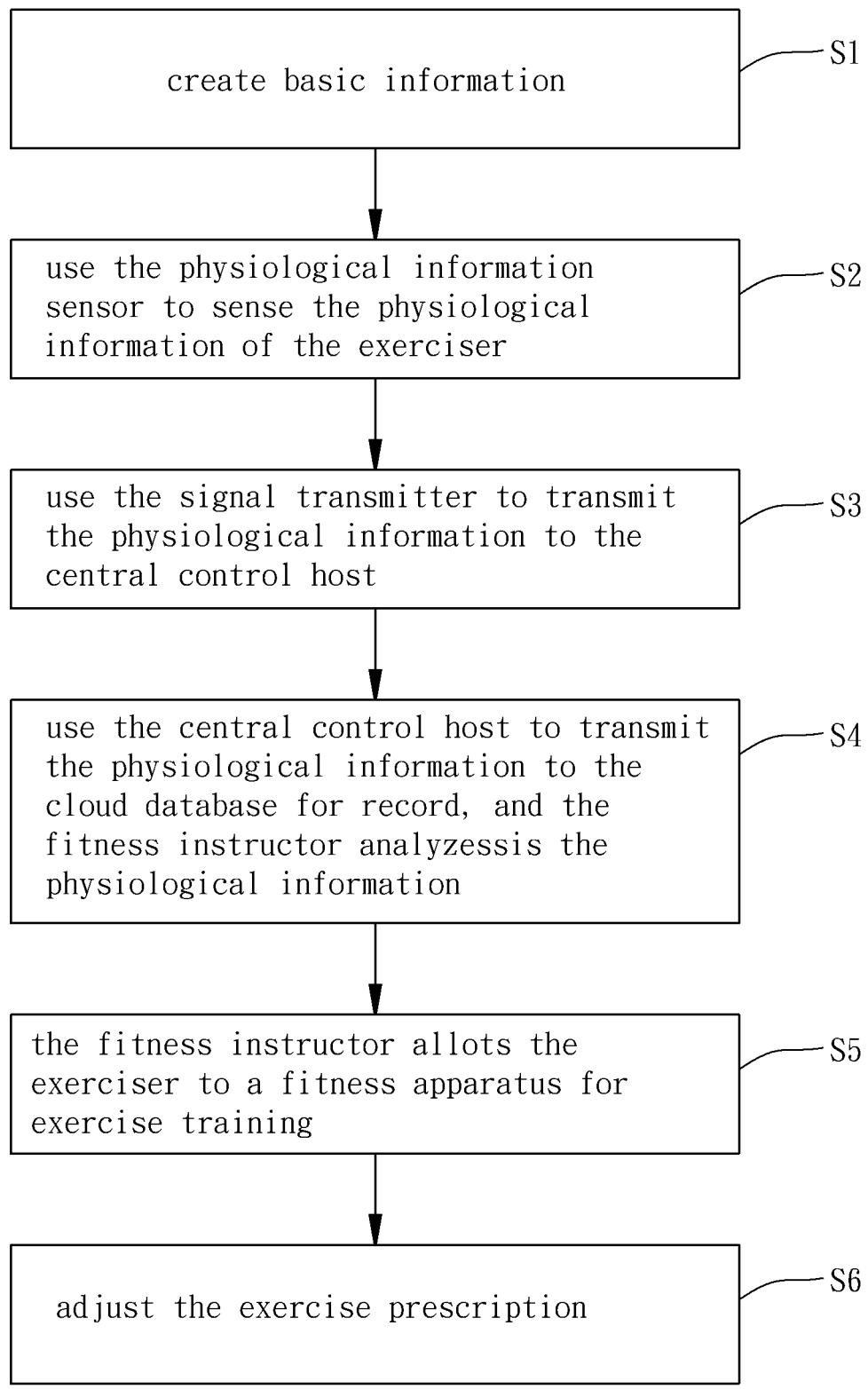
FIG. 3 is a flow chart of an assessing method provided by the intelligent exercise intensity assessing system of the present invention.

The structure of the intelligent exercise intensity assessing system 10 of the present invention is described above. The assessing method of the intelligent exercise intensity assessing system 10 of the present invention will be described below, as shown in the steps S1-S6 in FIG. 3.

At first, the exerciser 12 needs to create the basic information on the central control host 50 before the first time of training. The central control host 50 transmits the aforementioned basic information to the cloud database 60 for storage. In the next time of training, using a cellphone 14 to scan QR Code can bring out the previously created basic information from the cloud database 60, and there is no need to create it again. After the first creation of the basic information is accomplished, the cloud database 60 calculates the maximum heart rate of the exerciser 12 according to the basic information of the exerciser 12. Then let the exerciser 12 wear the physiological information sensor 30 and keep motionless for a period of time (about 3 minutes), and obtain the resting heart rate of the exerciser 12 by the physiological information sensor 30. Then let the exerciser 12 start operating the exercise testing machine 20 to perform the exercise test, so that the maximal oxygen uptake is obtained, and use the maximal oxygen uptake and the heart rate reserve to obtain the metabolic equivalent of task (MET) of the exerciser 12, so as to obtain the energy consumption of the exerciser 12 under different training intensity by the metabolic equivalent of task.

After the exerciser 12 operates the exercise testing machine 20 for a period of time, the system monitors the heart rate of the exerciser 12 in real time and uses a rating of perceived exertion scale (RPE scale) for storing self-feeling information corresponding to different heart rates of the exerciser 12 in the cloud database 60. For example, when the heart rate of the exerciser 12 doesn't attain the dangerous interval but the exerciser 12 has felt discomfortable or unwell, this information will be stored in the cloud database 60 for the monitoring of the exercise condition of the exerciser 12 and the providing of appropriate training intensity.

In this embodiment, the metabolic equivalent of task is calculated by the following equation: MET=VO2max× MHRR÷3.5÷60, wherein MET is the metabolic equivalent of task, VO2max is the maximal oxygen uptake, and MHRR is the maximum of the heart rate reserve under different training intensity. For example, referring to Table 1, in the condition that the maximal oxygen uptake of the exerciser is 41.2 ml/kg/min, when the exerciser exercises under the low-grade training intensity for 60 seconds, MET=(41.2× 0.39÷3.5÷60)×60 (seconds)=4.59; when the exerciser exercises under the medium-grade training intensity for 60 seconds, MET=(41.2×0.59÷3.5÷60)×60 (seconds)=6.95; when the exerciser exercises under the high-grade training intensity for 60 seconds, MET=(41.2×0.85÷3.5÷60)×60 (seconds)=10.01. In this way, when the three exercises of different training intensity are accomplished, it obtains Total MET=4.59+6.95+10.01=21.55.

Figure 4:
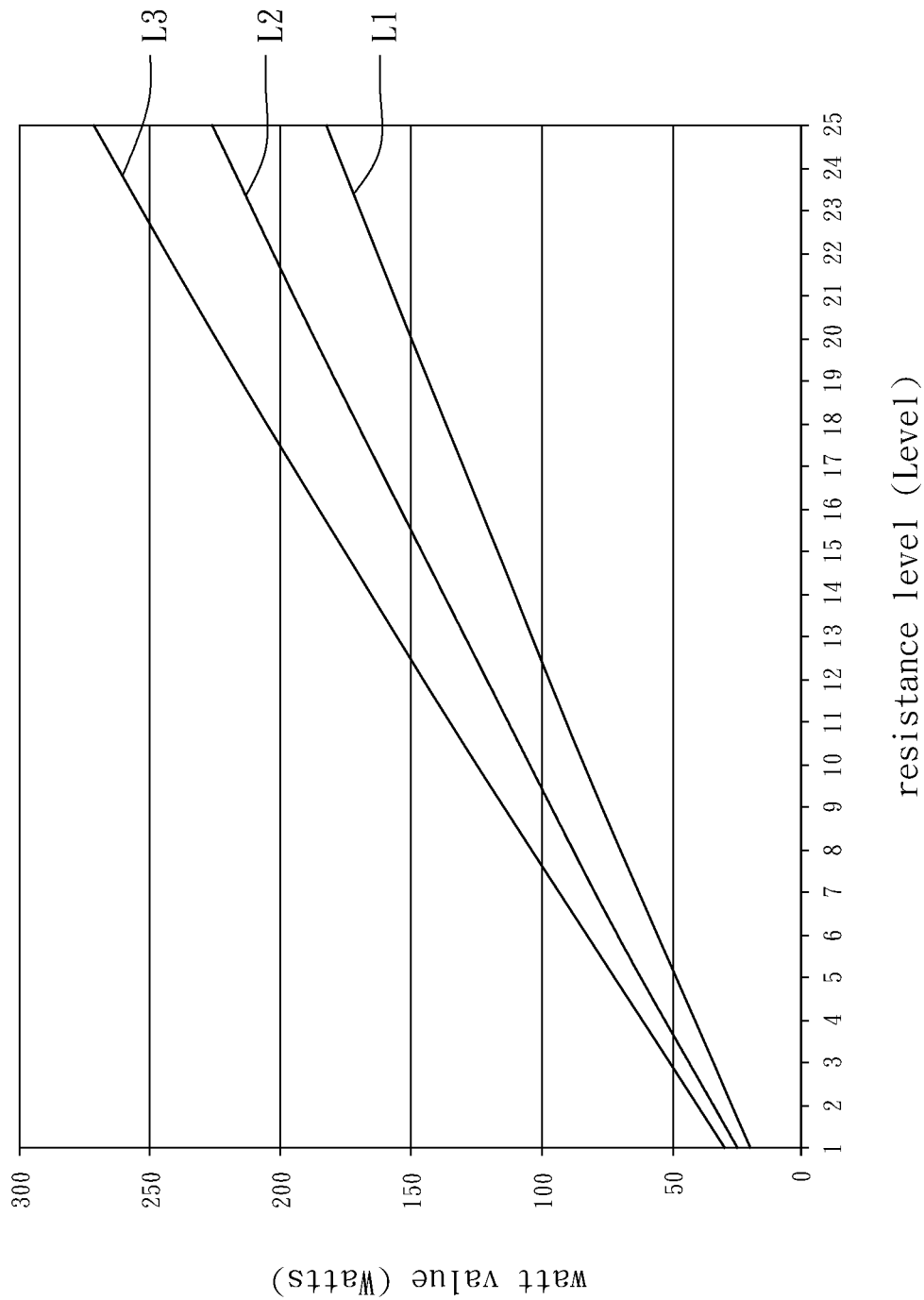
FIG. 4 is a curve graph of a watt value to a resistance level provided by the intelligent exercise intensity assessing system of the present invention.

On the other hand, after the exerciser 12 operates the exercise testing machine 20 for a period of time, the cloud database 60 obtains the forecasted watt values under different training intensity such as the warm-up grade, low grade, medium grade and high grade (referring to Table 1 and Table 2). Then referring to FIG. 4, the horizontal axis in FIG. 4 is the resistance level of the fitness apparatus, and the vertical axis in FIG. 4 is the watt value of the fitness apparatus. By contrasting the forecasted watt values obtained by the cloud database 60 with different curves shown in FIG. 4, the resistance levels of the fitness apparatus (taking an elliptical machine as an example hereinafter) under different rotary speeds are obtained. In this embodiment, the rotary speed corresponding to the curve L1 is 50 rpm, the rotary speed corresponding to the curve L2 is 60 rpm, and the rotary speed corresponding to the curve L3 is 70 rpm. For example, referring to Table 1, when the forecasted watt value is 49, contrasting it with the curve L2 in FIG. 4 obtains the resistance level ranged between 3 and 4, and wherein the larger resistance level is mainly taken. Besides, in Table 2, when the forecasted watt value is 95, contrasting it with the curve L2 in FIG. 4 obtains the resistance level ranged between 8 and 9, and wherein the larger resistance level is mainly taken.

After obtaining the resistance level, the cloud database 60 allots the exerciser 12 to an upright bike, elliptical machine, rowing machine or any exercise apparatus controllable in its rotary speed, resistance level or watt value, and controls the fitness apparatus used by the exerciser 12 to provide the corresponding resistance level for the exerciser 12 to perform the associated training. When the associated training is performed, the physiological information of the exerciser 12 will be all recorded and uploaded to the cloud database 60. According to the received data, the cloud database 60 assesses if the exercise prescription for the exerciser 12 needs adjustment, such as increasing or decreasing the resistance level or allotting the exerciser 12 to another fitness apparatus. For example, when it is discovered by the cloud database 60 that the forecasted watt value obtained under the same resistance level varies, such as in the condition that the resistance level is 9, the forecasted watt value dropping from 97 corresponding to the curve L2 to 78 corresponding to the curve L1, it represents that the physical ability of the exerciser decreases, resulting in decrease of the rotary speed of the fitness apparatus. Alternatively, in the condition that the resistance level is 9, if the forecasted watt value raises from 97 corresponding to the curve L2 to 117 corresponding to the curve L3, it represents that the physical ability of the exerciser increases, resulting in increase of the rotary speed of the fitness apparatus. In anyone of the above-described conditions, the cloud database 60 will adjust the resistance level according to the physiological information in real time to optimize the training effect of the exerciser, or the cloud database 60 will adjust the resistance level of the next use according to the physiological information. Besides, the exerciser 12 can intuitively see the physical ability condition thereof on the screen 42. As shown in FIG. 2, different color blocks are used on the screen 42 for distinguishing different training intensity. For example, blue (B) represents the warm-up grade, green (G) represents the low grade, yellow (Y) represents the medium grade, orange (O) represents the high grade, and red (R) represents the dangerous grade. In this way, through the color block distinguishing, the exerciser knows the training situation thereof more intuitively. When the exerciser 12 wants to lose weight positively, the system will lengthen the time in the orange (O) (high-grade intensity) block, or increase the resistance for the orange block to increase the intensity.

In conclusion, the intelligent exercise intensity assessing system 10 of the present invention can trace and record the exercise condition of the exerciser 12 for every time, and after analyzing the associated data, obtain the exercise prescription suitable for the exerciser 12 by calculation in coordination with the physiological information of the exerciser 12, so as to optimize the effect of the exercise training for the exerciser 12.

What is claimed is:

1. An intelligent exercise intensity assessing system comprising:
    an exercise testing machine for an exerciser to perform an exercise test;
    a physiological information sensor worn on the exerciser for sensing a physiological information of the exerciser before and after the exerciser operates the exercise testing machine;
    a signal transmitter electrically connected with the physiological information sensor for receiving the physiological information sensed by the physiological information sensor;
    a central control host electrically connected with the signal transmitter for collecting the physiological information received by the signal transmitter; and
    a cloud database electrically connected with the central control host for recording the physiological information and analyzing the physiological information, the cloud database using the physiological information to obtain a forecasted watt value corresponding thereto and obtain a resistance level corresponding to different fitness apparatuses according to the forecasted watt value;
    wherein the central control host is adapted for the exerciser to create a basic information; the central control host obtains a maximum heart rate of the exerciser from the basic information;
    wherein before the exerciser operates the exercise testing machine, the physiological information sensor obtains a resting heart rate of the exerciser; the cloud database calculates a heart rate reserve by the resting heart rate and the maximum heart rate, and uses the heart rate reserve to obtain a heart rate value of the exerciser under different training intensity;
    wherein the cloud database calculates the heart rate reserve as MHR is the maximum heart rate, RHR is the resting heart rate, HRR is the heart rate reserve, and MHR−RHR=HRR; when the training intensity is a warm-up grade, the heart rate value is RHR+(HRR× 20%); when the training intensity is a low grade, the heart rate value is RHR+(HRR×40%); when the training intensity is a medium grade, the heart rate value is RHR+(HRR×60%); when the training intensity is a high grade, the heart rate value is RHR+(HRR×85%).

2. The intelligent exercise intensity assessing system as claimed in claim 1, wherein the cloud database obtains the resistance level of the different fitness apparatuses under different rotary speeds according to the forecasted watt value; when the forecasted watt value obtained by the cloud database under the same resistance level varies, the cloud database adjusts the resistance level.

3. The intelligent exercise intensity assessing system as claimed in claim 2, wherein the cloud database adjusts the resistance level in use according to the physiological information in real time.

4. The intelligent exercise intensity assessing system as claimed in claim 2, wherein the cloud database adjusts the resistance level of a next use according to the physiological information.

5. The intelligent exercise intensity assessing system as claimed in claim 1, wherein when the exerciser operates the exercise testing machine, the cloud database uses a rating of perceived exertion scale (RPE scale) to obtain physical condition of the exerciser under different heart rates; after the exerciser operates the exercise testing machine, the cloud database obtains a maximal oxygen uptake of the exerciser, and uses the maximal oxygen uptake and the heart rate reserve to obtain a metabolic equivalent of task (MET) of the exerciser; the metabolic equivalent of task is calculated by a following equation: MET=VO2max×MHRR÷3.5÷60, wherein MET is the metabolic equivalent of task, VO2max is the maximal oxygen uptake, and MHRR is a maximum of the heart rate reserve under different training intensity.

6. The intelligent exercise intensity assessing system as claimed in claim 1, wherein the exercise testing machine is an exercise bike.

7. An assessing method of the intelligent exercise intensity assessing system as claimed in claim 1 comprising the steps of:
    a) using the physiological information sensor to sense the physiological information of the exerciser before and after the exerciser operates the exercise testing machine;
    b) using the signal transmitter to receive the physiological information and transmit the physiological information to the central control host;
    c) using the central control host to transmit the physiological information to the cloud database for analysis, so that the cloud database obtains said forecasted watt value corresponding thereto and obtains said resistance level corresponding to different fitness apparatuses according to the forecasted watt value; and
    d) using the cloud database to allot the exerciser to one of the fitness apparatuses and control the fitness apparatus used by the exerciser to provide the resistance level obtained in the step c).

* * * * *